United States Patent [19]

Puskas et al.

[11] 4,002,648
[45] Jan. 11, 1977

[54] CATALYZED TRANS-ACIDOLYSIS REACTION OF TRIMELLITIC ACID, TRIMELLITIC ANHYDRIDE AND 2-NAPHTHOIC ACID

[75] Inventors: Imre Puskas, Glen Ellyn; Ellis K. Fields, River Forest, both of Ill.

[73] Assignee: Standard Oil Company, Chicago, Ill.

[22] Filed: Sept. 8, 1975

[21] Appl. No.: 611,534

Related U.S. Application Data

[60] Continuation-in-part of Ser. No. 379,202, July 16, 1973, abandoned, Division of Ser. No. 63,622, Aug. 13, 1970, Pat. No. 3,784,573.

[52] U.S. Cl. .................. 260/346.3; 260/455 R; 260/469; 260/475 N; 260/475 P; 260/475 PN; 260/475 R

[51] Int. Cl.² ........................................ C07D 307/89

[58] Field of Search ........ 260/485 R, 475 R, 346.3, 260/475 PN, 475 P, 476, 469, 410.9 N, 455 R, 475 N

[56] References Cited

UNITED STATES PATENTS

| | | | |
|---|---|---|---|
| 3,182,073 | 5/1965 | Loncrini | 260/346.3 |
| 3,714,234 | 1/1973 | White | 260/486 R |

FOREIGN PATENTS OR APPLICATIONS

| | | | |
|---|---|---|---|
| 1,181,198 | 11/1964 | Germany | 260/346.3 |

OTHER PUBLICATIONS

Fieser, et al., Advanced Organic Chem., N.Y.–Reinhold Pub. (1961), p. 358.

*Primary Examiner*—Henry R. Jiles
*Assistant Examiner*—Bernard Dentz
*Attorney, Agent, or Firm*—William C. Clarke; Arthur G. Gilkes; William T. McClain

[57] ABSTRACT

The trans-acidolysis reaction between carboxylic acids and lower alkanoic acid esters of organic hydroxy or mercapto compounds is catalyzed by Group I*a* and II*a* metal salts of alkanoic acids such as sodium acetate.

4 Claims, No Drawings

CATALYZED TRANS-ACIDOLYSIS REACTION OF TRIMELLITIC ACID, TRIMELLITIC ANHYDRIDE AND 2-NAPHTHOIC ACID

This application is a continuation-in-part of application Ser. No. 379,202, filed July 16, 1973, now abandoned which in turn is a division of application Ser. No. 63,622, filed Aug. 13, 1970. now U.S. Pat. No. 3,784,573.

This invention relates to the use of new catalysts in trans-acidolysis reactions. The reaction can be illustrated, using monofunctional reactants, by the following equation:

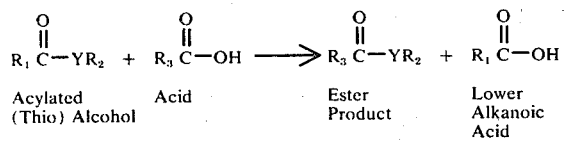

| $R_1\overset{O}{\underset{\|}{C}}-YR_2$ + | $R_3\overset{O}{\underset{\|}{C}}-OH$ | $\longrightarrow$ | $R_3\overset{O}{\underset{\|}{C}}-YR_2$ + | $R_1\overset{O}{\underset{\|}{C}}-OH$ |
|---|---|---|---|---|
| Acylated (Thio) Alcohol | Acid | | Ester Product | Lower Alkanoic Acid | where Y is oxygen or sulfur. The lower alkanoic acid product is removed by distillation, and the equilibrium consequently is shifted to the right.

We have discovered that the trans-acidolysis reaction between carboxylic acids and lower alkanoic acid esters of organic hydroxy or mercapto compounds (also referred to collectively hereinafter as "alcohols") is catalyzed by certain bases. The bases that we have found effective are the basic metal carboxylates, in particular the acetates and stearates of Group Ia and IIa metals of the periodic table. The active species in these compounds is the anion and we have found that such anions are effective for catalyzing the reaction between broad classes of both carboxylic acids and lower alkanoic acid esters of hydroxy- or mercapto-compounds.

Sulfuric acid, p-toluenesulfonic acid, magnesium, lithium, and sodium have been reported to be catalysts for various trans-acidolyses, other than the trans-acidolysis of trimellitic anhydride. When p-toluenesulfonic acid, zinc chloride and aluminum chloride were employed in the method of this invention for the reaction of hydroquinone diacetate and trimellitic anhydride, they did not produce a significant increase in the reaction rate. On the other hand, any basic metal carboxylate can be used and will be broadly applicable to trans-acidolysis reactions — i.e. these anionic catalysts will not be specific to only certain narrow classes of coreactants -so long as they are derived from acids whose dissociation constants are less than $10^{-4}$. Particularly effective catalysts of this type are the alkali and alkaline earth acetates and stearates. Such catalysts include sodium and potassium acetate and stearate. While the anhydrous salt of these catalysts are effective, we have also found that their hydrated forms possess enhanced catalytic properties. This can be seen by comparing the performance of anhydrous sodium acetate with its trihydrate and the monohydrate of calcium acetate with the tetrahydrate of magnesium acetate in Table 1.

As pointed out above, the anionic catalysts of this invention are effective over a broad range of co-reactants. Generally the prior art has utilized trans-acidolysis in the synthesis of monoesters, diesters, triesters and long chain polyesters suitable for fiber and film applications. The anionic catalysts of this invention are suitable for each of these applications. Heretofore, when these important trans-acidolyses were carried out, either in the absence of catalysts or with less effective catalysts than those of the present invention, besides the longer reaction time per se being disadvantageous, the prolonged exposure to reaction temperatures degraded the products, frequently causing severe discoloration. One expedient adopted to ameliorate the problem was to conduct the reaction in a solvent which, while not preventing the discoloration, facilitated the separation of the discolored products. Using either of our catalyst-types, these reactions are so rapid that high yields can be obtained without discoloration. This, in turn, permits our reaction to be run in the absence of solvent, thus making our process comparatively inexpensive vis-a-vis raw material cost and solvent-processing costs.

The metal carboxylate catalysts of the present invention are added to the reaction mixture from an external source and are not formed in situ from precursors.

Where the desired product is a monoester, the monobasic carboxylic acid susceptible to our anionic catalysis may be a mononuclear aromatic monocarboxylic acid such as benzoic, o-toluic, m-toluic, p-toluic; a fused ring aromatic acid such as 1-naphthoic, 2-naphthoic, 1-napthylacetic, beta-1-napthyl-propionic acid, 1- and 2-naphthyacrylic acids; anthracene-1-carboxylic acid, anthracene-2-carboxylic acid, etc. among the aliphatic acids suitable are the alkanoic acids such as propionic, n-buteric, n-valeric and higher homologues such as capric, stearic, and melissic. Alkenoic acids may be used, having mono- or poly-unsaturation, such as acrylic, 9-octadecenoic, 9,12-octadecadienoic, 9,12,15-octadecatrieneoic, 13-docosenoic and the like. Cycloalkanoic and cycloalkenoic acids are useful and include cyclohexane carboxylic, tetrahydrobenzoic, decahydronaphthoic and cyclohexaneacetic acids.

The anionic catalysts of the present invention also promote the reaction between those co-reactants known by the prior art to be useful in preparing polyanhydrides. The carboxylic acids used therein are tricarboxylic acids and include trimellitic anhydride, trimellitic acid, 1,2,4-naphthalene tricarboxylic acid, 1,4,8-naphthalene tricarboxylic acid, 1,2,4-butane tricarboxylic acid, 1,2,3-benzene tricarboxylic acid, 1,2,3-propane tricarboxylic acid and 2,3,6-naphthalene tricarboxylic acids and their corresponding anhydrides.

The anionic catalysts of the present invention are further useful in catalyzing the trans-acidolysis reaction between co-reactants useful in the preparation of long-chain polyesters. Useful acids include both aliphatic and aromatic dicarboxylic acids. Illustrative of these are alkanedioic acids, alkenedioic acids and aromatic dicarboxylic acids. Exemplary of the alkanedioic acids are oxalic, malonic, succinic, glutaric, adipic, and higher homologues such as sebacic; among the alkenedioic acids are maleic and fumaric. The aromatic acids include: o-phthalic, isophthalic, terephthalic; the homophthalic or carboxy-phenylacetic acids such as o-carboxy-phenylacetic, m-carboxy-phenylacetic, p-carboxy-phenylacetic; and the phenylenediacetic acids such as o-, m-, p-phenylenediacetic, o-phenyleneacetic-propionic, o-, m-, p-phenylenedipropionic, and p-phenylenediisobutyric acid.

The second co-reactant useful in our trans-acidolysis reactions is a lower alkanoic acid ester of a hydroxide- or mercapto-containing compound. These lower alkanoic acids and their use in trans-acidolysis processes are well known to the art. Since they are reformed in the course of the trans-acidolysis reaction as unwanted by-products, the preferred lower alkanoic acids are those with low boiling points, which property facilitates their removal by distillation. Such acids include formic, acetic, propionic, butyric, benzoic, and the like. These acids are used to acylate the alcohols of the present invention. Again, the selection of the type of alcohol will depend on whether the end product of the trans-acidolysis reaction desired is a monoester, diester, etc. When a monoester is desired any monoalkanol or its corresponding thiocounterpart may be used. Primary, secondary and tertiary alcohols may be used although primary alcohol is preferred. Among the saturated monohydric alcohols that are useful are n-butyl, isobutyl sec-butyl, and higher members of the series such as n-myristyl and n-stearyl; corresponding alkenols are likewise useful. The aromatic compounds phenol and thiophenol may be used and are included, for the purpose of describing our invention, in the term "alcohol."

Polyalcohols useful in the present invention have the following general formula:

$$R - (Y)_n$$

where Y is -OH or -SH; n-2 to 4: and R is a phenylene radical, a fused, carbocyclic with 4 rings or less, a biphenyl, a terphenyl, a bis-phenylene, or a straight chain aliphatic radical. Among the useful polyalcohols containing the phenylene radical are hydroquinone, resorcinol; providing the fused carbocyclic structure are such compounds as dihydroxy naphthalene, trihydroxy naphthalene and dihydroxy anthracene; dihydroxy biphenyl typifies the bi-phenyl compounds. The bis-phenylene radicals have the following structures:

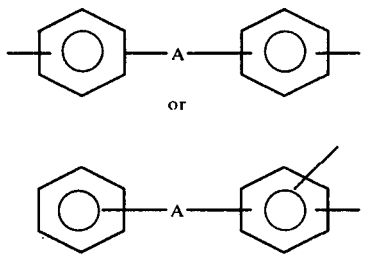

where A is any of the following divalent radicals: $C_1$-$C_3$ alkylene, sulfonyl, carbonyl, thio or oxy. Dihydroxy compounds providing the above bis-phenyl structure include dihydroxybenzophenone; 4,4'-isopropylidenediphenol (Bisphenol A); 4,4'-isobutylidenediphenol (Bisphenol B); 4,4'-isopropylidenedi(o-cresol) (Bisphenol C); p,p'-methylenebiphenol.

The R group of the polyalcohol may also be an aliphatic radical. Exemplary of such compounds would be a glycol such as ethylene glycol, diethylene glycol, polyethylene glycol, neopentyl glycol, 1,6-hexanediol, such higher homologues as 1,20-eiconsanediol and 1,22-docosanediol; and such higher polyhydroxy compounds as glycerol, pentaerythritol and the like. The aliphatic chain may also have ether linkages within it as illustrated by such compounds as the polyether and polyester polyols well known in the urethane foam art.

The catalyzed-transacidolyses reactions of the present invention are, generally speaking, carried out under substantially the same conditions used in the prior art.

Specifically, the mole ratio of the acylated alcohol to the carboxylic acid is not critical to this improved process of transacidolysis. It will depend of course on the type of product desired. Selection of suitably ratios th achieve the various products is well known to the art. Temperatures range from 100°–350° C; higher temperatures, say 280°–300° C, being most preferred when phenols are used.

The anionic catalysts of this invention have diminished activity in solvents of the chlorinated-aromatic type. For example, sodium acetate was not an effective catalyst for the reaction of trimellitic anhydride with hydroquinone diacetate in chlorinated polyphenol (Arochlor 1248, a product of Monsanto) solution. The most preferred medium is a mixture of the co-reactants themselves. At the higher temperatures of transacidolysis all the co-reactants enumerated hereinabove will be above their melting points and the trans-acidolysis is conveniently and cheaply carried out in the melt phase. Preferably the reaction is conducted under an inert-gas blanket such as nitrogen, but this precaution is not essential.

The minimum effective concentration of our catalysts has not been determined but appreciable activity can be seen at a concentration of about 0.005 moles catalyst per mole of carboxylic acid.

The following examples will illustrate the practice of the invention. Such examples are illustrative only and in no way do we intend to imply that they are co-extensive with the scope of this invention.

0.25 moles of an acylated alcohol (Table 1 below) was mixed with 0.50 mole of a carboxylic acid (Table 1) and 0.005 mole of a catalyst of this invention (Table 1). The mixture was placed in a 500 ml three-necked flask equipped with a mechanical stirrer, thermometer, and Dean-Stark trap joined to a graham condenser, and heated by a silicone oil bath. After the mixture melted, stirring was begun. Temperature was maintained as indicated (Table). The reactions were terminated at various stages of completion as indicated by the formation of by-product acetic acid which was being monitored. Products were recovered from the melt by pouring the hot reaction mixture into warm acetic acid. The products crystallized, were filtered and then washed with a chlorobenzene-benzene mixture and were dried. Analyses revealed the products to be carboxylic acid esters. First-order rate constants were calculated from experimental data and are used herein as a measure of catalytic effect.

TABLE 1

| Series No./Example No. | Acylated Alcohol | Carboxylic Acid[6] | Catalyst[6][2] | $k_1$ | Temp. °C | Medium | Product |
|---|---|---|---|---|---|---|---|
| 1-1 | HDQ | TMA | None | 0.0047[1] | 277 | Melt | Bis-Trimellitate |
| 1-2 | " | " | NaAc | 1.18[1] | " | Melt | " |
| 2-3 | " | " | None | 0.0097 | 260 | Melt | " |
| 2-4 | " | " | NaAc | 0.0870 | " | Melt | " |
| 2-5 | " | " | NaAc . 3 $H_2O$ | 0.0920 | " | Melt | " |
| 2-6 | " | " | KAc | 0.0990 | " | Melt | " |
| 2-7 | " | " | $CaAc_2 . H_2O$ | 0.122 | " | Melt | " |
| 2-8 | " | " | $MgAc_2 . 4H_2O$ | 0.158 | " | Melt | " |

TABLE 1-continued

| Series No./Example No. | Acylated Alcohol | Carboxylic Acid[1] | Catalyst[6x2] | $k_1$ | Temp. °C | Medium | Product |
|---|---|---|---|---|---|---|---|
| 3-9 | HDQ | TMA | None | 0.0109 | 317 | Arochlor 1248[5] | '' |
| 3-10 | '' | '' | Na Stear | 0.0122 | '' | '' | '' |
| 4-11 | BP-A | '' | None | 0.0108 | 260 | Melt | '' |
| 4-12 | '' | '' | NaAc | 0.0392 | '' | Melt | '' |
| 4-13 | '' | '' | NaAc[3] | 0.0869 | '' | Melt | '' |
| 5-14 | 4-ABP | '' | None | 0.0166 | 270 | Melt | Mono-Trimellitate |
| 6-15 | '' | 2-NA | None | 0.0255 | 256 | Melt | 2-naphthoate |
| 6-16 | '' | '' | Na Stear[4] | 0.118 | '' | Melt | '' |
| 6-17 | '' | '' | NaAc[4] | 0.152 | '' | Melt | '' |
| 7-18 | '' | IPA | None | 0.0404 | 270 | Melt | isophthalate |

[1]Calculated as initial third order rate constants.
[2]At 0.5 mole % based on moles of acid unless otherwise noted.
[3]1.5 mole %
[4]2.0 mole %
[5]T.M. of Monsanto Co. for chlorinated-biphenyls.
[6]Reactant and catalyst abbreviations: HDQ = Hydroquinone diacetate; BP-A = Bisphenol-A diacetate; 4-ABP = 4-Acetoxybiphenyl; TMA = Trimellitic anhydride; 2-NA = 2-Naphthoic acid; IPA = Isophthalic acid; NaAc = Sodium acetate; KAc = potassium acetate; and NaStear = Sodium stearate.

We claim:

1. In the method of reacting a lower alkanoic monoester of an alcohol selected from the group consisting of n-butyl alcohol, isobutyl alcohol, sec-butyl alcohol, higher monoalkanols up to n-stearyl alcohol, the corresponding alkenols and the corresponding thiols or a lower alkanoic polyester of a polyalcohol having the formula $$R-(Y)_n$$

where Y is -OH or -SH, n is 2 to 4, and R is a phenylene radical, a fused carbocyclis with 4 rings or less, a biphenyl, a terphenyl, a bisphenylene or a straight chain aliphatic radical with an organic acid selected from the group consisting of trimellitic acid, trimellitic anhydride and 2-naphthoic acid, as the reaction mixture in a trans-acidolysis reaction, the improvement comprising conducting the reaction in the presence of an effective amount of a basic metal carboxylate catalyst, in the liquid melt phase and in the absence of solvent, said catalyst being a carboxylate of a metal selected from the group consisting of sodium, potassium, calcium and magnesium, the said carboxylate having a $K_B$ less than $10^{-4}$ and said carboxylate being added to the reaction mixture from an external source.

2. The method of claim 1 wherein the carboxylate is selected from the group consisting of an acetate and a stearate.

3. The method of claim 2 wherin the carboxylate is an acetate.

4. The method of claim 2 wherein the carboxylate is a stearate.

* * * * *